United States Patent
Von Bünau et al.

(10) Patent No.: US 12,295,661 B2
(45) Date of Patent: May 13, 2025

(54) COMBINATION DEVICE FOR TONOMETRICAL MEASURING AND DRUG APPLICATION ON AN EYE

(71) Applicants: Carl Zeiss AG, Oberkochen (DE); Carl Zeiss Meditec, Inc., Dublin, CA (US)

(72) Inventors: Rudolf Murai Von Bünau, Jena (DE); Johannes Kindt, Weimar (DE); Martin Hacker, Jena (DE); Tobias Bühren, Ulm (DE); Thomas K. Fitzmorris, Palo Alto, CA (US); Daniel Bublitz, Rausdorf (DE); Steffen Wagner, Jena (DE); Wibke Hellmich, Jena (DE)

(73) Assignees: Carl Zeiss Meditec, Inc., Dublin, CA (US); Carl Zeiss AG, Oberkochen (DE)

( * ) Notice: Subject to any disclaimer, the term of this patent is extended or adjusted under 35 U.S.C. 154(b) by 1091 days.

(21) Appl. No.: 17/047,346

(22) PCT Filed: Apr. 29, 2019

(86) PCT No.: PCT/EP2019/060862
§ 371 (c)(1),
(2) Date: Oct. 13, 2020

(87) PCT Pub. No.: WO2019/211217
PCT Pub. Date: Nov. 7, 2019

(65) Prior Publication Data
US 2021/0145278 A1 May 20, 2021

Related U.S. Application Data

(60) Provisional application No. 62/664,750, filed on Apr. 30, 2018.

(51) Int. Cl.
*A61B 3/16* (2006.01)
*A61B 3/00* (2006.01)
(Continued)

(52) U.S. Cl.
CPC .............. *A61B 3/16* (2013.01); *A61B 3/0033* (2013.01); *A61F 9/0026* (2013.01); *G16H 20/10* (2018.01); *A61B 2562/245* (2013.01)

(58) Field of Classification Search
CPC ... A61B 3/16; A61B 3/0033; A61B 2562/245; A61B 3/165; A61F 9/0026; A61F 9/0008; G16H 20/10; A61M 35/00
(Continued)

(56) References Cited

U.S. PATENT DOCUMENTS 3,640,274 A   2/1972   Costello
3,915,564 A   10/1975  Urban
(Continued)

FOREIGN PATENT DOCUMENTS

DE   102011114753 A1   4/2013
EP       1701652 B1     9/2006
(Continued)

OTHER PUBLICATIONS

International Search Report and Written Opinion for International Patent Application No. PCT/EP2019/075770 mailed on Sep. 18, 2019, 19 pages.
(Continued)

*Primary Examiner* — Tuyen Tra
(74) *Attorney, Agent, or Firm* — Snell & Wilmer L.L.P

(57) ABSTRACT

The proposed combination device combines any tonometric metrology with a drug application to administer glaucoma medication on an eye. Several technical concepts are proposed and exemplary embodiments for rebound tonometry and air-puff tonometry are shown. However other methods such as optical coherence elastography (OCE) could also be used. The Solutions provide home care tonometry offerings which host the capability to administer glaucoma medication.

42 Claims, 10 Drawing Sheets

(51) Int. Cl.
*A61F 9/00* (2006.01)
*G16H 20/10* (2018.01)

(58) Field of Classification Search
USPC .................................................. 351/200, 205
See application file for complete search history.

(56) References Cited

U.S. PATENT DOCUMENTS

| | | | |
|---|---|---|---|
| 7,768,652 | B2 | 8/2010 | Everett |
| 7,854,510 | B2 | 12/2010 | Verdooner et al. |
| 8,012,136 | B2 | 9/2011 | Collins et al. |
| 8,488,895 | B2 | 7/2013 | Muller et al. |
| 9,087,145 | B2 | 7/2015 | Ballou et al. |
| 10,314,740 | B2 * | 6/2019 | Kraft .................. G07F 17/0092 |
| 2004/0267108 | A1 | 12/2004 | Moore |
| 2009/0275924 | A1 | 11/2009 | Lattanzio et al. |
| 2011/0060208 | A1 | 3/2011 | Gur |
| 2011/0234977 | A1 | 9/2011 | Verdooner |
| 2012/0022505 | A1 | 1/2012 | Dacquay et al. |
| 2012/0022506 | A1 | 1/2012 | Rickard et al. |
| 2014/0228783 | A1 | 8/2014 | Kraft |
| 2016/0374555 | A1 | 12/2016 | Kontiola et al. |
| 2017/0049323 | A1 | 2/2017 | Bublitz et al. |
| 2018/0014727 | A1 | 1/2018 | Bublitz et al. |

FOREIGN PATENT DOCUMENTS

| | | |
|---|---|---|
| JP | 2014528793 | 10/2014 |
| JP | 2017038944 | 2/2017 |
| WO | WO-2013043607 A1 | 3/2013 |
| WO | WO-2017223341 A1 | 12/2017 |

OTHER PUBLICATIONS

JPO; Notice of Reasons for Refusal dated Jun. 6, 2023 in Japanese Application 2020560814.
JPO; Search Report dated May 12, 2023 in Japanese Application 2020560814.
EPO, Office Action dated Jan. 7, 2022 in EP Serial No. 19721253.3.
EPO, Office Action dated Jul. 4, 2022 in EP Serial No. 19721253.3.

* cited by examiner

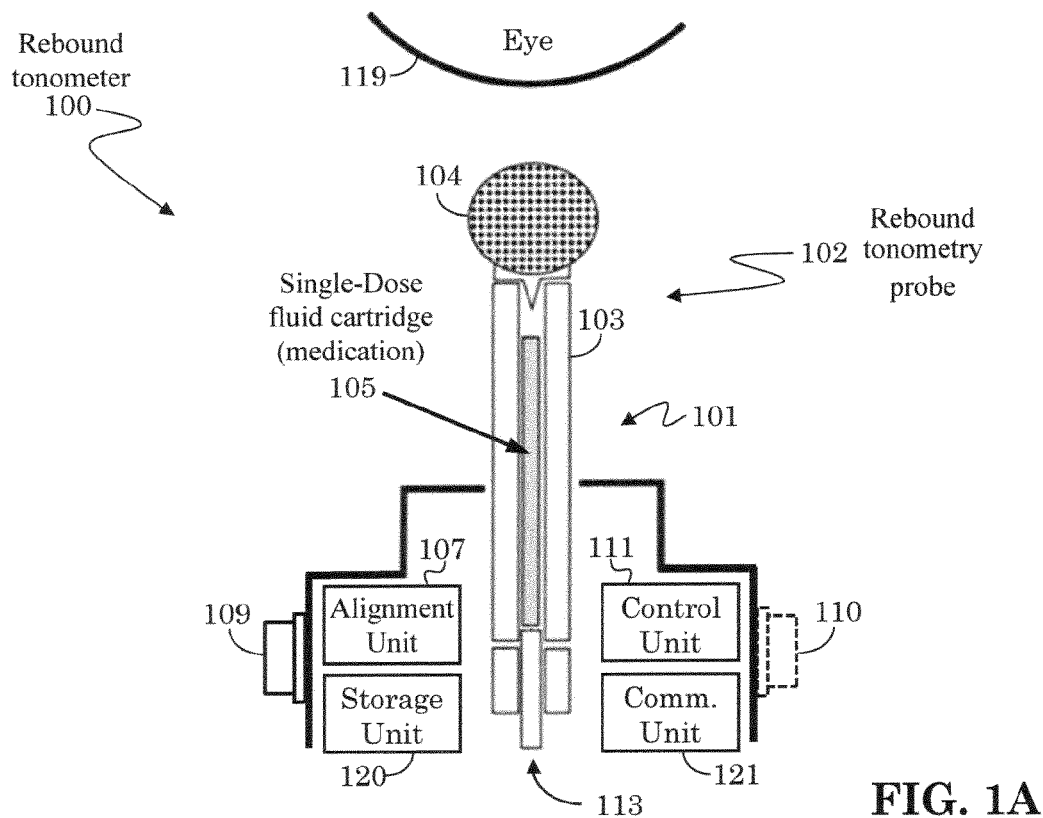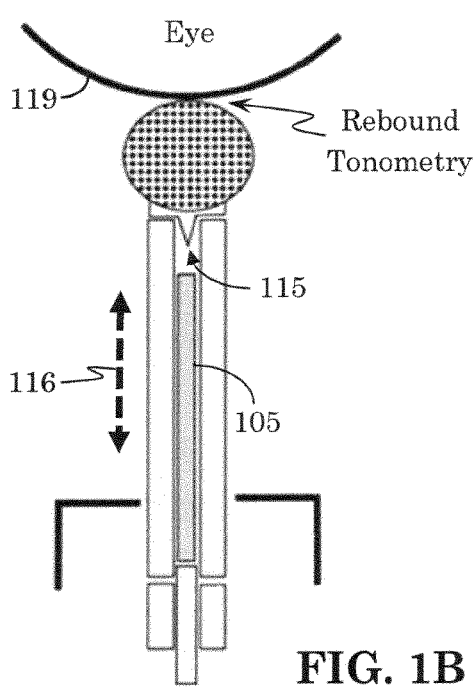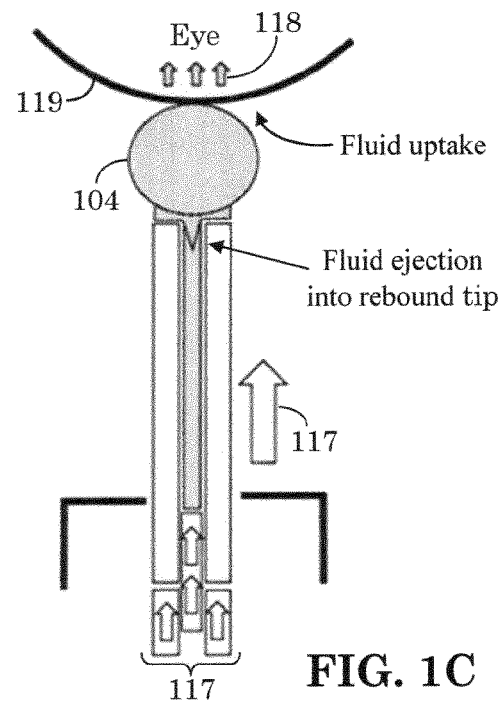
FIG. 1A
FIG. 1B
FIG. 1C

| | Rebound Tonometry | |
|---|---|---|
| Medication | Multi-dose Drops (Smart cartridge) 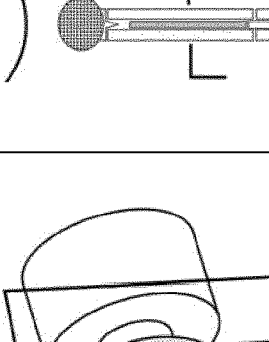 | Unit-dose Drops (Disposable-IOP Probe/plunger)  |
| Interface | | |
| Interface for medication | specific smart cartridge interface (incl. License key) | Proprietary rebound probe/tip/plunger interface (incl. proprietary plunger interface) |
| IOP measurement and drug delivery | Separate medication cartridge and IOP probe/plunger | IOP probe/plunger combined with single dose medication |
| Smartphone/Tablet/Smart-glasses connection including two way real time or near real time data transfer between health care provider and patient and/or third party | √ | √ |
| Home care scheduler | | |
| Medication Intake and IOP reminder / selector | √ | √ |
| Medication type selector / dosing | √ | √ |
| Medication intake counter | √ | √ |
| Separate IOP measurement & medication intake possible | √ | √ |
| Other | | |
| Proof of delivery | √ | √ |
| Precision dosage | √ | √ |
| Proof of Patient ID | √ | √ |
| IOP dependent custom dosage | √ | — |
| Automatic medication trigger while eye is open | √ | √ |
| Diurnal IOP data can be integrated | √ | √ |

Table 1

FIG. 9

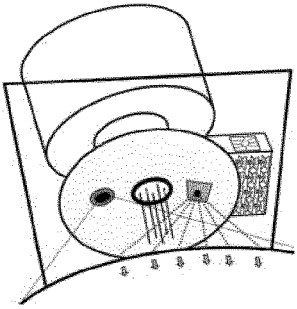

FIG. 10 — Table 2

| | Air-Puff Tonometry | |
|---|---|---|
| | Multi-dose Drops (Smart cartridge) | Unit-dose Drops (Single-dose magazine) |
| Medication | | |
| Interface | | |
| Interface for medication | Specific smart cartridge interface (licensable) | Specific smart cartridge interface (licensable) |
| IOP measurement and drug delivery | Separate medication cartridge and IOP channel | Separate medication cartridge and IOP channel |
| Smartphone/Tablet/Smart-glasses connection including two way real time or near real time data transfer between health care provider and patient and third party | ✓ | ✓ |
| Home care scheduler | | |
| Medication Intake and IOP reminder / selector | ✓ | ✓ |
| Medication type selector / dosing | ✓ | ✓ |
| Medication intake counter | ✓ | ✓ |
| Separate IOP measurement and medication intake possible | ✓ | ✓ |
| Other | | |
| Proof of delivery | ✓ | ✓ |
| Precision dosage | ✓ | ✓ |
| Proof of Patient ID | ✓ | ✓ |
| IOP dependent custom dosage | ✓ | ✓ |
| Automatic medication trigger while eye is open | ✓ | ✓ |
| Diurnal IOP data can be integrated | ✓ | ✓ |

| | Multi-dose Drops (Smart cartridge) | Air-Puff Tonometry Unit-dose Drops (Single-dose magazine) | Multi-dose Drops (Standard Medication bottle) |
|---|---|---|---|
| Medication | | | |
| Interface | | | |
| Interface for medication | specific smart cartridge interface (licensable) | Specific smart cartridge interface (licensable) | Generic medication bottle interface |
| IOP measurement and drug delivery | Same medication cartridge and IOP channel | Same medication cartridge and IOP channel | Same medication cartridge and IOP channel |
| Smartphone/Tablet/Smart-glasses connection including two way real time or near real time data transfer between health care taker and patient and third party | ✓ | ✓ | ✓ |
| Home care scheduler | | | |
| Medication Intake and IOP reminder / selector | ✓ | ✓ | ✓ |
| Medication type selector / dosing | ✓ | ✓ | ✓ |
| Medication intake counter | ✓ | ✓ | |
| Separate IOP measurement and medication intake possible | ✓ | ✓ | ✓ |
| Other | | | |
| Proof of delivery | ✓ | ✓ | |
| Precision dosage | ✓ | ✓ | |
| Proof of Patient ID | ✓ | ✓ | ✓ |
| IOP dependent custom dosage | ✓ | ✓ | ✓ |
| Automatic medication trigger while eye is open | ✓ | ✓ | ✓ |
| Diurnal IOP data can be integrated | ✓ | ✓ | ✓ |

Table 3

FIG. 11

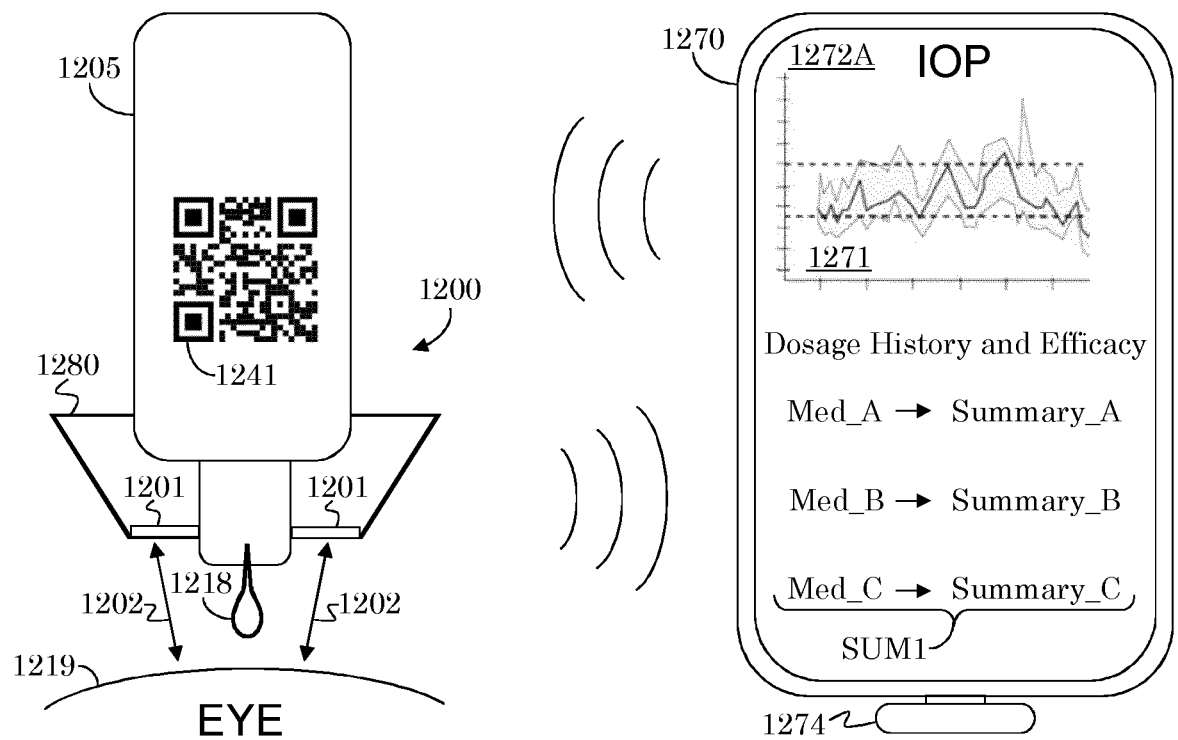
FIG. 12
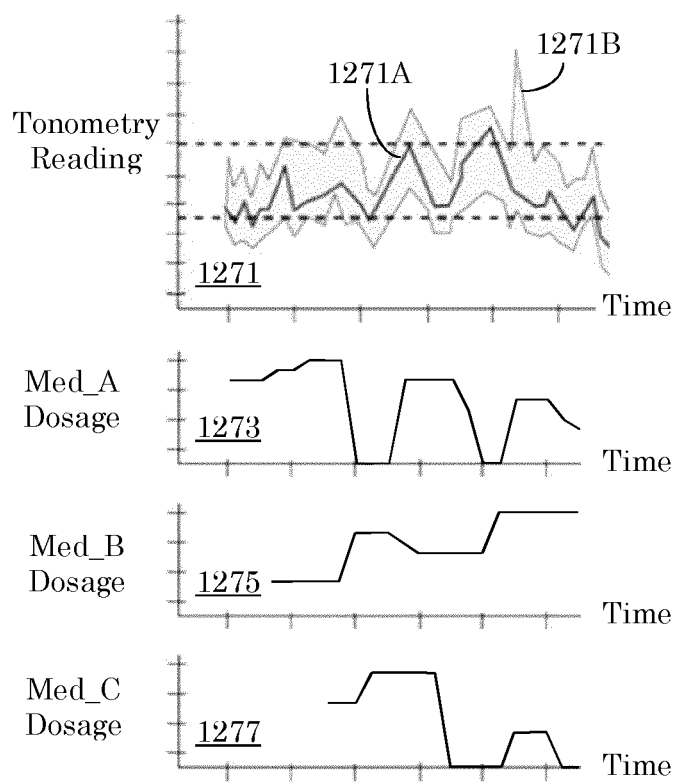
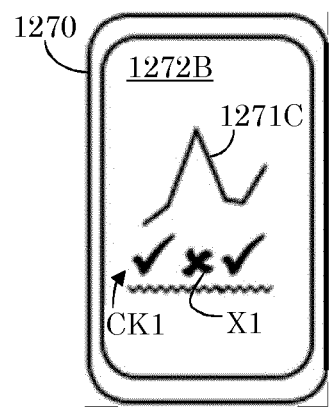
FIG. 13

COMBINATION DEVICE FOR TONOMETRICAL MEASURING AND DRUG APPLICATION ON AN EYE

PRIORITY

This application is a National Phase application under 35 U.S.C. § 371 of International Application No. PCT/EP2019/060862, filed Apr. 29, 2019, which claims priority to U.S. Provisional Application Ser. No. 62/664,750, filed Apr. 30, 2018, the contents of which are hereby incorporated by reference in their entirety.

FIELD OF INVENTION

This invention generally relates to tonometers for measuring the pressure in an eyeball. More specifically, it relates to a combination device that provides tonometrical measurements and drug administration to an eye.

BACKGROUND

Tonometrical measurements for monitoring the pressure in an eye (intraocular pressure) is of particular interest to patients suffering from glaucoma. A glaucoma or green cataract is the excavation (excision) of the optic nerve. This typically results in steadily progressing damage to the optic nerve, which causes an equally steady reduction of the visual field of a patient. Without therapy, this generally results in complete loss of eyesight. Although the exact cause of glaucoma or damage to the optic nerve has not yet been fully elucidated, an increase in intraocular pressure due to worsened aqueous humor drainage in the eye has been identified as a likely trigger. Therefore, continuous monitoring of intraocular pressure is of great importance in the treatment of such patients.

Drop application (e.g. medication application) and intraocular pressure (IOP) measurement (e.g., tonometry) at home are, per se, independent modalities of glaucoma care. Both require vigilant and continuous patient adherence, along with fine motor skills, over many years, as one typically lives with the disease into an advanced age. For IOP measurement, at least an increase in the frequency of periodic measurement would be desirable when a change in disease management is instigated in order to monitor its efficacy. This could be implemented via home monitoring in a convenient and cost-effective manner, whereas even annual measurements of diurnal IOP variation pose a high burden on cost when performed at a health-care center (e.g., clinic) rather than in a home care setting.

Self-administered medication, in particular drop application, has been shown to have poor patient adherence and unsuccessful drop administration outcomes. The global increase of chronic disease (along with its associated burden on health care systems and related efforts to install telemedicine and home monitoring eco-systems) will likely increase demand for patient self-management, and thereby increase demand for vigilant and continuous patient adherence.

Home monitoring technologies for some chronic diseases exist, such as self-intraocular pressure measurement (self-IOP) units (e.g., self-tonometers) for patients with glaucoma. For example, the Icare® HOME tonometer permits IOP self-monitoring. It is designed for home use for glaucoma patients, who need regular IOP monitoring, as determined by an ophthalmologists. This device is based on a rebound measuring principle, in which a probe (e.g., a rod) moves in-and-out to rebound repeatedly, but softly, on an eyeball (e.g., the rod tip, or rebound tip, is softly applied to the eyeball and allowed to bounce back) to measure intraocular pressure. This is a handheld device that a patient may use to self-administer an IOP measurement anytime, since it requires no eye drops or pressurized air source or other specialized equipment or skills. This permits IOP monitoring outside a clinic, which provides more information to the ophthalmologist and comfort to the patient. Additional information on the Icare® HOME tonometer may be found at the Internet home webpage of Icare Finland, a part of Revenio Group Corporation, a public company listed on the Helsinki Stock Exchange.

Alternative IOP home measurement concepts have been suggested, such as described in patent EP 1701652 B1. This patent describes a non-contact tonometer for measuring the intra-ocular pressure of an eye by projecting light into the eye and measuring the reflected light as affected by mechanical distortion. The cornea is distorted by delivering a pneumatic pulse. The tonometer consists mainly of an electro-optical unit mountable on the head of a user and a control unit. The control unit of the tonometer includes a display and optionally a buzzer, such as to audibly alert the user to a measurement failure or if a battery is low. The electro-optical unit employs a tubular wave guide, a light detector, and a reflector for deflecting a light beam to the eye and for eliminating a part of the reflected light reaching the detector. The aligning of the tonometer with the head of the user is optionally assisted by an observed reticle.

Another non-contact tonometer approach is provided in US. Pub. 2016/0374,555, which uses a source for producing mechanical waves of several frequency from a distance to the eye. The source may be an electromagnetic source, e.g. a laser source, or an acoustic source. A detector, such as an optical interferometer, then detects at least one surface wave from a distance from the eye, which may then be used to determine pressure information, such as by use of a mode map (e.g. frequency-velocity chart of traveling waves) based on intra-ocular pressure.

Methods for monitoring adherence to glaucoma medication are also known. For example, U.S. Pat. No. 8,012,136 B2 describes an ophthalmic fluid delivery device adapted to deliver an ophthalmic fluid in the form of a mist to an ocular region of a patient. The ophthalmic fluid delivery device includes a nozzle having an aperture through which the ophthalmic fluid can flow and at least one shutter positioned proximate to the aperture of the nozzle. The shutter is mounted for movement with respect to the aperture of the nozzle between an open position permitting flow of the ophthalmic fluid through the aperture of the nozzle, and a closed position at least partially covering the aperture. A shutter actuator is positioned proximate to the shutter and coupled to the shutter such that the movement of the shutter actuator moves the shutter between the open position and the closed position.

Concepts of digital medication administration and monitoring based on Piezo technology are also known. For example, U.S. Pat. No. 9,087,145 B2 describes a solution for delivering a medicament to an eye of a subject in need thereof. The method may include: (a) providing droplets containing the medicament with a specified average size and average initial ejecting velocity; and (b) delivering the medicament to the eye, where the droplets deliver a percentage of the ejected mass of the droplets to the eye.

US Pub. 2014/0228783 A1 describes a portable drug dispenser, which includes one or more chambers for holding multiple separately contained drug products, a dispensing mechanism for accurately dispensing one or more of the separately contained drugs upon activation of the dispensing mechanism in a specified dose (e.g. specified volume/number of drops) at specified times, and a processor configured to determine the time, and potentially other information such as, e.g., location, patient variables, user data input of each activation of the dispensing mechanism. The portable drug dispenser may further transmit the determined time of activation to a computer located remote to the dispenser, or optionally store the information on the device, to be read by a clinician managing the patient. The user may also provide data inputs, such as intra-ocular pressure, visual acuity and other visual measures, vital signs, e.g., as measured by external measurement devices, which may include wearable devices on the patient that measure heart rate, blood pressure, and/or activity, and may further include optional built in accelerometer or data derived from sensors in a mobile phone or other networked device which communicates with the dispenser.

It is an object of the present invention to provide a solution that combines both home care modalities (self-administered medication and IOP measurement) in one simple process step.

It is a further object of the present invention that the one simple process also be customizable as needed (i.e. pressure-measurement only, or medication-application only, or both combined).

SUMMARY OF INVENTION

The above objects are met in tonometer that incorporates a medication dispensing unit. That is, a combined tonometer and medication applicator is provided. In accordance with the present invention, any tonometry technique may incorporate medication application (e.g., drop application) to administer glaucoma medication. The medication dispensing unit may be a separate unit integrated into the tonometer (separate from a tonometry measurement unit within the tonometer housing) and apply medication separately from the taking of a tonometry measurement. Alternatively, the mediation dispensing unit may be more fully integrated into the tonometer and make use of the tonometry measurement unit. That is, the medication dispensing unit may utilize the pressure sensing mechanism of the tonometer to apply medication to an eye. For example, in the case of a rebound-based tonometer that uses a mechanical probe (e.g., rod tip, or rebound tip) to repeatedly probe (e.g., touch) an eye, after (or optionally during) the tonometric measurement is complete, medication may be applied to the same tip of the probe so that medication is applied to the eye as the probe touches the eye. As another example, in the case of an air-puff-based tonometer, the medication may be sprayed by the same air-puff (or same air-puff mechanism) used to take the tonometric measurement. Thus, medication may be applied singularly in one independent process step and a tonometric measurement taken separately in another independent process step, or both medication administration and tonometry measurement may be executed together in one combined step. This one combined step may apply medication while the tonometry measurement is being taken, or the combined step may be comprised of two sub-steps executed in sequence. For example, in a first sub-step, one action is taken (e.g., tonometry measurement) followed immediately by the other sub-set (medication application), both being executed in response to a single measure-and-medicate command/sequence.

Although examples of using rebound tonometry and air-puff tonometry are provided, it is to be understood that the present invention may be applied to other methods of tonometry, such as optical coherence elastography (OCE). Thus, the present invention contemplates incorporating medication application/dispensation into OCE.

The present invention also provides multiple home care tonometry options for administering glaucoma medication. Such options may include a disposable one-way pressure/medication probe for medication application, or a license fee model for smart cartridges that can be used via a cartridge license key for the present combined tonometer and medication applicator. An important aspect of the present invention is the ability to guide a patient in therapy, and to monitor medication and/or IOP pressure measurements during home care. This may be achieved via two-way real time, or near real time, data transfer between a patient and a responsible health care provider and/or third parties.

Other objects and attainments together with a fuller understanding of the invention will become apparent and appreciated by referring to the following description and claims taken in conjunction with the accompanying drawings. All references mentioned in the present text are respectively incorporated in their entirety by reference.

The embodiments disclosed herein are only examples, and the scope of this disclosure is not limited to them. Any embodiment feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIGS. 1A-1C illustrate a rebound tonometry tip with single dose glaucoma medication in its rod, for use in a rebound-based tonometer. The tonometer's rod and tip are used as integral parts of a medication application unit to apply medication.

FIG. 9 illustrates a Table 1 that lists functionalities that may be enabled with a rebound tonometry unit, such as those illustrated in FIGS. 1 and 2.

FIG. 10 illustrates a Table 2 that lists functionalities which may be enabled in an air-puff tonometer having a separate (non-contact) drug administration unit, such as illustrated in FIGS. 3 and 4.

FIG. 11 illustrates a Table 3 that lists functionalities which may be enabled in an air-puff tonometer, whose own air-puff is used to administer medication (such as illustrated in FIGS. 5, 6, and 7) so that a separate drug administration unit is not necessary.

FIG. 12 illustrates another embodiment of a combination device for tonometry and drug administration along with an example application for improved monitoring of IOP measurements and for better assessment of a medication's effectiveness.

FIG. 13 illustrate the monitoring and comparing of IOP measurements and applied medication dosages.

DESCRIPTION OF THE PREFERRED EMBODIMENTS

Figure 2:
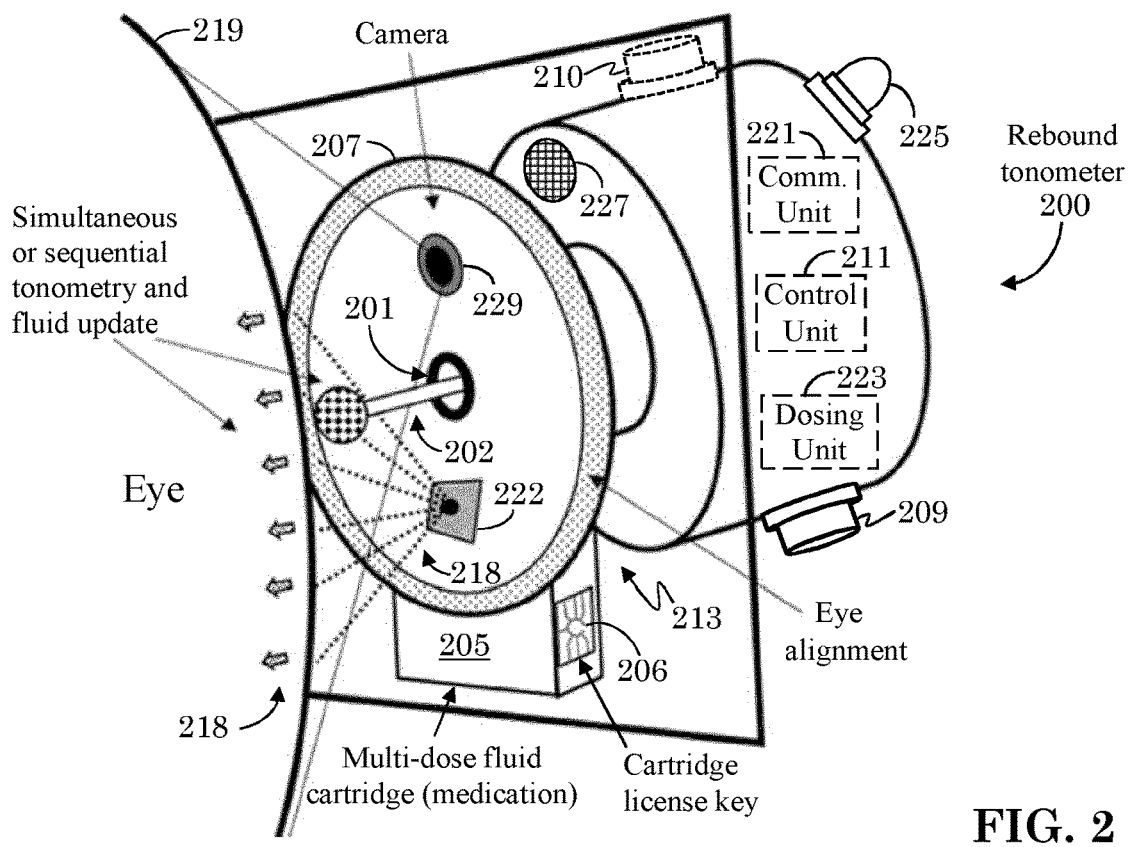
FIG. 2 illustrates a rebound tonometer with a separate medication application mechanism/unit that uses a smart cartridge to apply medication separately from the tonometer's rod.

The present invention incorporates a medication dispensing unit (medication applicator) into a tonometry measuring unit (e.g., a unit used to measure intraocular pressure, or pressure in the eye). The tonometry measuring unit may be based on any known tonometric technology, such as a rebound-based tonometer, air-puff-based tonometer, electromagnetic-based or acoustic-based mechanical wave tonometer, optical coherence elastography (OCE), etc. By way of example, and not limitation, the present invention is described below as applied to a rebound-based tonometer and an air-puff-based tonometer. The incorporated medication dispensing unit may be independent of the tonometry measuring unit/mechanism of the tonometer or may incorporate parts of the tonometry measuring unit/mechanism (e.g., be integral to the tonometry measuring unit). That is, the medication dispensing unit may make use of a tonometry measuring mechanism to apply medication in predefined doses. For illustration purposes, separate examples of a rebound-based tonometer and an air-puff-based tonometer, each separately illustrated with an integral medication application dispenser and with an incorporated, but independent, medication application dispenser, are provided below.

The case of a rebound-based tonometer whose tonometry mechanism integrates a medication dispensing unit is addressed first. More specifically, a first example provides a combination device for tonometric measurements and drug application on an eye. FIG. 1A illustrates the tip (e.g., application side) of an exemplary rebound tonometer 100, which uses a rebound tonometry probe 102, which oscillates back-and-forth against the cornea 119 of an eye to obtain a measure of the eye's intraocular pressure (IOP). The tonometry probe 102 may be disposable/replaceable, and typically consists of a tonometer's rod 103 and tip 104. In the present case, the tonometer's rod 103 and tip 104 are used as integral parts of a medication application/delivery unit 113 to apply medication to the cornea 119. The rebound tonometer 100 includes a rebound tonometer mechanism as measuring unit 101, which may include rebound tonometry probe 102 (e.g., rod 103 and rebound tip 104), an alignment unit 107 to align the rebound tonometry probe to the eye, at least one user-actuated trigger (e.g., control button 109, or a switch, touch screen, or optical sensor) for triggering tonometry measurement and/or drug application, and a control unit 111 for interfacing with (e.g., for controlling) the various units (including a data storage unit 120 and communication unit 121). Alignment unit 107 helps to properly position the rebound tonometer 100 and establish a predefined distance between the measuring unit 101 and the patient's eye. Alignment unit 107 may include a concave mirror that a patient views for self-alignment, a camera, a guidance arm that extends to and contacts a predefined region(s) of a patient's face (e.g., forehead and/or cheek), a distance sensor based on electromagnetic waves, etc. Data storage unit 120 may store IOP measurements, times when medication was applied, dosage of applied medication, and/or one or more treatment plans provided by a medical practitioner with prescribed times and dosage for IOP measurements medication application. Optionally, data storage unit 120 may be integral to communication unit 121 and/or distributed across multiple memory spaces. Communication unit 121 may support both wired and wireless communication and provide communication links with various electronic devices, such as smart phones, tablet computers, personal computers, portable (e.g. flash or thumb) memories, etc.) Communication unit 121 may transfer data stored in storage unit 120 to any of these electronic devices (e.g., for presentation or transmission to a health care provider or database) or may receive data for updating storage unit 120 (e.g., updating a treatment plan. In the present embodiment, the medication application unit 113 is an integral part of the tonometry mechanism. For example, the medication application unit 113 may include a single dose fluid cartridge 105 with medication inside (such as glaucoma medication) housed within the tonometer's rod 103. Rebound tonometer 100 may take a tonometry reading and apply a medication dosage (either simultaneously or sequentially) in response to a single input command (e.g., button 109). Optionally, two control buttons (e.g., button 109 and an optional second button 110) may be provided for respective, separate triggering of tonometric measurement and drug administration. In a typical rebound-based (e.g., dynamic or impact) tonometer, analysis of motion parameters of the bouncing tonometry probe 102 after colliding with the cornea 119 is applied (such as by control unit 111) to determine an IOP measure. If necessary, this analysis may be extended to take into account the single dose fluid cartridge 105 within tonometer's rod 103. If desired, in the case where medication is applied while taking the tonometry reading, the motion analysis may further take into the account the transfer of medication from the single dose fluid cartridge 105 through the tip 104 to the eye while the tonometry measurement is being taken.

In summary, a rebound tonometer 100 is herein proposed which contains a single dose cartridge 105 of glaucoma medication within the rod 103 (or tip 104) of the tonometry probe/plunger 102. FIG. 1A illustrates the tip of a rebound tonometer 100 with single dose glaucoma medication 105 in its rod 103 along with a mechanism to separately apply tonometry and medication in a single process step. Use of a single or unit dose medication cartridge has the advantage of allowing preservative free drugs. As with standard rebound tonometry, the tonometry probe/plunger 102 is sealed in a sterile fashion. Similarly, the single dose medication 105 located in the rod 103 (or tip 104) of the tonometry probe/ plunger 102 is also sealed. Depending on the measurement mode of the device 100 (i.e. tonometry or medication application, or both) different mechanisms apply, that result in one simple process step.

FIGS. 1B and 1C illustrate an exemplary implementation of a medication application mechanism suitable for the tonometer of FIG. 1A. After the tonometry probe/plunger 102 has been unsealed and attached to the rebound tonometry device 100, the tonometry measurements may be captured in the standard fashion, e.g., using a fast tonometry measurement sequence, as illustrated by dash arrow 116 in FIG. 1B Immediately at the end of the fast tonometry measurement sequence, a mechanism (e.g., that presses fluid cartridge 105 against a puncturing tip 115) may automatically break a medication seal of the single dose fluid cartridge 105 and releases medication to the surface of the rebound tip 104 (as indicated by wide arrows 117 in FIG. 1C). At this point, one or a few more "measurement" oscillation movements of the rebound tip 104 touching the eye releases the medication to the cornea 119 (as indicated by shaded arrows 118 in FIG. 1C). This process step is a short extension within a few added milliseconds to the original tonometry measurement so that it is not perceived as an extra step of action for the user. Each of the process steps can also be executed independently by a smart scheduler concept.

In an alternate embodiment, the rebound tonometry probe 102 could include a rod and a balloon-type (e.g., bladder) tip filled with a single medication dose. The tonometry measurement could still done in the standard fashion, but in the last contact (or last few rebound contacts) of the balloon-type tip against the cornea, the medication filled tip (balloon-type tip) is made to burst so that the medication moistens the eye.

Furthermore, it is possible to load the single dose rebound probes into a magazine, so that no manual step for loading the device 100 with a probe/plunger 102 is required and sterility is ensured.

As another example, FIG. 2 illustrates a rebound tonometer 200 with a medication application mechanism/unit 213 housed within the tonometer housing but separate from a tonometry measuring unit 201. This combination device 200 for tonometric measurerments and drug application on the eye may include a typical rebound tonometer mechanism (e.g., use a rebound tonometer probe 202 as described above in reference to the rebound tonometry probe 102 of FIG. 1A) as part of the measuring unit 201 separate from the medication application unit 213. The medication application unit 213 may use a single dose (fluid) cartridge or a multi-dose (fluid) cartridge as a drug reservoir 205. For illustration purposes, the rebound tonometer 200 of FIG. 2 shows a multi--dose (fluid) cartridge as the dmg reservoir 205. The medication application unit 213 may further include a dosing unit 223, which may be internal to rebound tonometer 200, for controlling a dosage amount per medication application step, such as by selecting a number of medication doses extracted from reservoir 205 to be applied during a medication application step. The medication application unit 213 may further include a non-contact dmg administration unit 222, which may spray medication 218 onto the eye, In the present example, tonometer 200 uses a concave mirror 207 as an alignment unit, at least one control button 209 for triggering tonometric measurement and/or drug application, and a control unit 211 with a first memory space (not shown) for storing data of the measurements and/or medication and a second memoly space for storing a treatment plan for the measurements and the medication. It is to be understood that both first and second memory spaces may be integrated into a single memory unit (e.g., electronic or optical memory) or span across multiple memory units. Optionally, two control buttons (e.g., button 209 and an optional second button 210) may be provided for respective, separate triggering of tonometric measurement and drug administration, as discussed above. The combination device 200 may additionally have a visual unit 225 (e.g., LED or electronic display) and/or an audio unit 227 (e.g., speaker) for respective visual and/or audible prompting of the patient to cany out a planned measurement and/or drug administration. The concave mirror 207 is positioned to provide a reflection of the eye visible to a patient to help the patient align the combination device 200 to the eye.

Furthermore, the combination device 200 may have a camera unit 229 for identifying the patient, identifying the patient's right and left eye, for controlling the orientation of the combination device 200 to the eye, and/or for controlling or determining a suitable state of the eye (e.g., opened or closed) for the tonometric measurement and drug administration. The left eye may be distinguished from the right eye by the noting the corners and shape of the eye. For example, identifying (e.g., the location of) the caruncle (e.g., the part corner of the eye closest to the nose) within an image may provide a convenient way to distinguish a left eye from or a right eye. This determination may be made by a specialized algorithm or by a machine learning model.

The combination device 200 may also have a communication unit 221 based on wired interface (e.g., communication cable) or wireless interfaces (e.g., wireless network, Bluetooth communication, radio frequency identification, RFID, etc.) for transferring the data stored in the control unit 211 to (local or remote) PCs, tablets, mobile memories (e.g., a portable flash memory, portable optical disk, and/or Internet-accessible online memory storage), or smart devices such as mobile telephones or smart-glasses (e.g., via the Internet). The combination device 200 may further have a cleansing unit (not shown) for rinsing and/or sterilizing the combination device 200, in particular its parts that come into contact with an eye, e.g., the tip of rebound tonometer probe 202. The cleansing unit may include, for example, a sterilizing pad, wash, or spray. As another example, if the combination includes 200 a cover for storage (not shown), the cleansing sterilizing pad, wash, or spray may be housed within the cover and come into contact with the tip when the cover is coupled to the combination device 200.

Optionally, the reservoir cartridge 205 may be a smart cartridge (e.g., a cartridge having an integrated circuit, IC, 215 with a contact interface (e.g., contact pads) or a non-contact interface (e.g., RFID, Bluetooth, or wireless network) which may be administered via a separate technical mechanism (e.g., a separate electronic controller). The smart cartridge may provide a cartridge license key, for example.

In summary, FIG. 2 illustrates a rebound tonometer 200 with a separate medication application mechanism 213 via smart cartridge 205. The cartridge 205 may be triggered immediately after a tonometry measurement is finished. A proof of delivery mechanism, e.g., via the camera 229, ensures that the eye is open while medication is being applied. In the present embodiment, medication is administered by spraying (via non-contact drug administration unit 222) the dosed drug from the multi-dose cartridge 205 on the cornea 219 of the eye. The cartridge 205 may be triggered immediately after a tonometry measurement is finished, and the proof of delivery mechanism via the camera 229 ensures that the eye is open while medication is applied.

Some functionalities enabled with the rebound tonometry embodiments of FIGS. 1A-1C and FIG. 2 are listed in Table 1 of FIG. 9. For example, both support simultaneous or separate (e.g., sequential) IOP measurement and dmg delivery operation. Both may provide a reminder mechanism to alert a patient to a prescheduled medication application or IOP measurement operation. Both provide mechanisms for different medication type selection, and for different dosing options. Although the multi-dose cartridge embodiment of FIG. 2 supports custom dosage, adjustment, while the unit-dose cartridge of FIGS. 1A-1C does not. Nonetheless, both embodiments provide a counter to track medication intake/application, a mechanism for proof of delivery of medication, precision dosage, mechanism for proof of patient ID (e.g., such as by use of a cartridge license TD and/or camera), and an mechanism to trigger automatic medication application while eye is open (e.g., such as by use a camera to monitor the open/close state of an eye).

Figure 3:
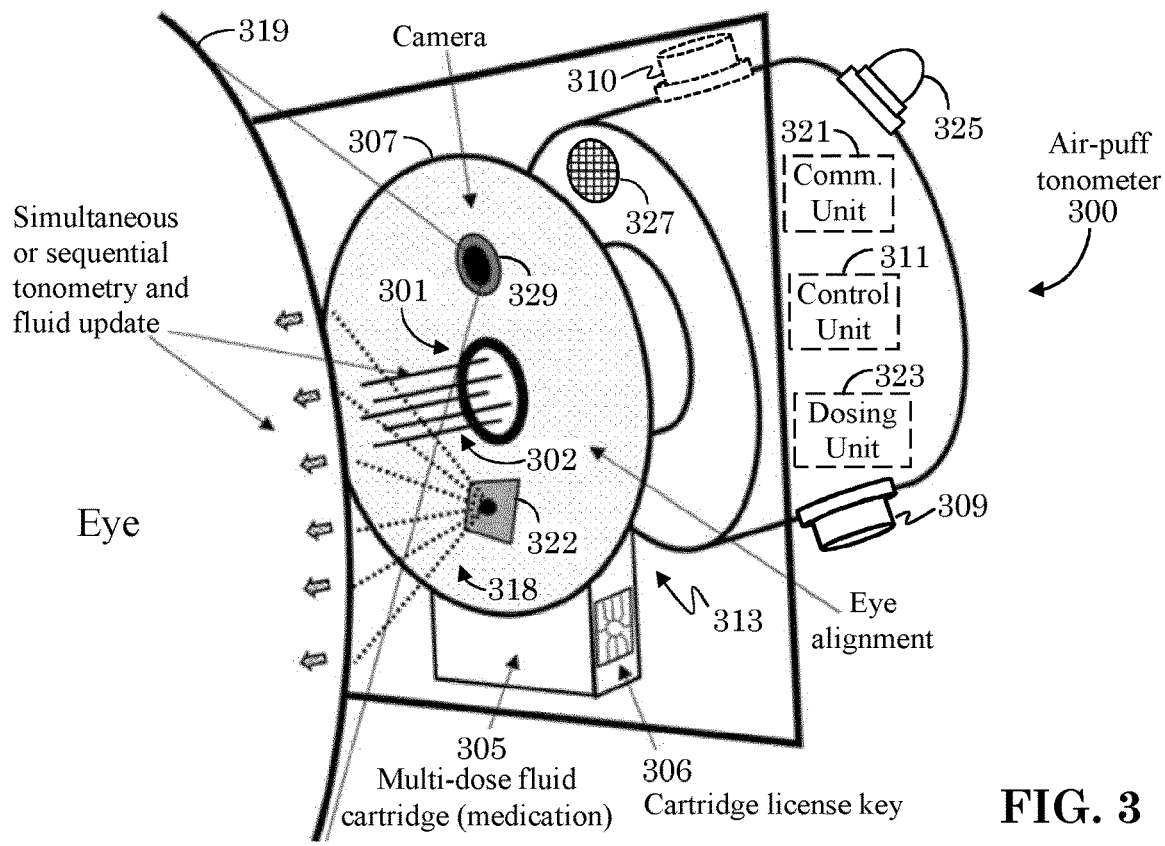
FIG. 3 illustrates an air-puff tonometer with a separate medication application unit that uses a multi-dose smart cartridge for glaucoma medication application, including a cartridge license key mechanism.

As is illustrated in FIG. 3, the present invention may also be incorporated into an air-puff tonometer 300, which applies a puff of air 302 to the cornea 319 of an eye and determines a measure of intraocular pressure (IOP) based on the resultant amount of cornea deformation, which may be observed by a combination of a light emitter and light detector (not shown) and/or camera 329. The present exemplary air-puff tonometer 300 uses a multi-dose smart cartridge 305 for glaucoma medication application, including a cartridge license key mechanism 306. Because a multi-dose cartridge 305 is used, a dosing unit 323 may be used to control/adjust medication dosage on a per medication application step. As shown, the medication applicator 313 may use a separate non-contact drug administration unit 322 (e.g., to spray medication 318 onto the eye) combined with an air-puff tonometer measuring unit 301. Like in the case of rebound tonometer 200 of FIG. 2, and as is explained above, the present air-puff tonometer 300 of FIG. 3 may include an alignment unit 307 (e.g., concave mirror), control unit 311, a first control button 309, an optional second control button 310, a camera unit 329, a visual unit 325 (e.g., LED or electronic display), and an audio unit 327 (e.g., speaker).

In summary, a preferred combination device 300 for tonometric measurements and drug application on the eye may include an air-puff tonometer as measuring unit 301, a drug reservoir 305, a non-contact drug administration unit 322, a concave mirror as alignment unit 307, at least one control button 309 for triggering the measurement and/or drug application, and a control unit 311 with (or with access to) a memory (not shown) for storing data of the measurements and/or medication and a memory (not shown) for storing a treatment plan for the measurements and the medication. The combination device 300 has additionally a visual unit 325 and/or audible unit 327 for prompting of the patient to carry out a planned measurement and drug administration. Furthermore the combination 300 device has additionally a camera unit 329 for identifying the patient, his right and/or left eye, for controlling the orientation of the combination device 300 to the eye and/or for controlling a suitable state of the eye (e.g., opened or closed) for the measurement and drug administration, and also a communication unit 321 for transferring the data stored in (or controlled by) the control unit 311. Communication unit 321 may be based on wired or wireless interfaces to PCs, tablets, mobile memories or even mobile telephones or smart-glasses. In the present embodiment, the drug reservoir 305 is a multi-dose cartridge, so that an additional dosing unit 323 may be used.

Figure 4:
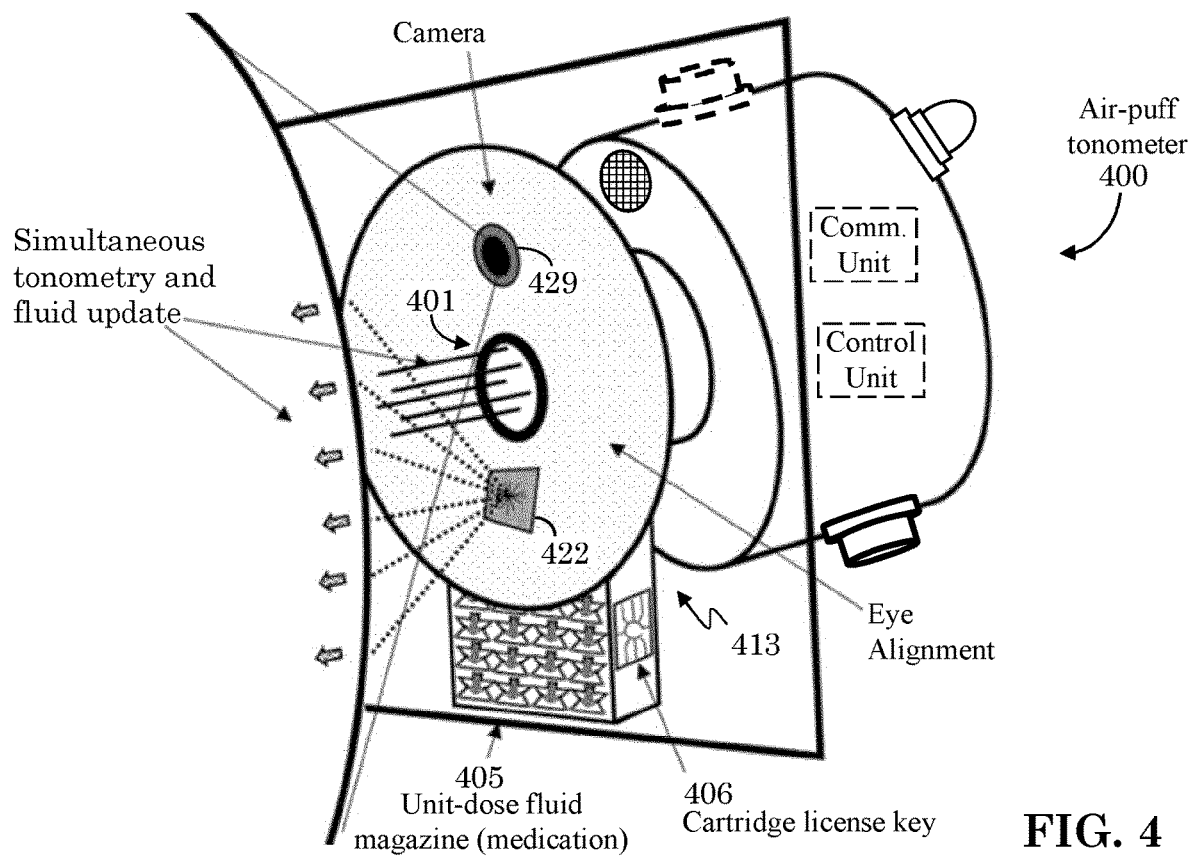
FIG. 4 illustrates an air-puff tonometer with a separate medication application unit that uses a unit-dose smart cartridge for glaucoma medication application, including a cartridge license key mechanism.

FIG. 4 illustrates a second embodiment for this design (e.g., air-puff tonometer 400), which is similar to that of FIG. 3 but with the drug reservoir implemented as a unit-dose cartridge, or magazine, 401 so that no dosing unit is not required. All other elements are similar to those described in reference to FIG. 3, unless otherwise state.

FIG. 4 illustrates air-puff tonometer 400 with unit-dose smart cartridge 405 (e.g., for glaucoma medication application) including a cartridge license key mechanism 406. As shown, the medication applicator 413 uses a separately non-contact drug administration unit 422 and is combined with the air-puff tonometer measuring unit 401.

A multi-dose cartridge 305 (FIG. 3) or a magazine of unit-dose cartridges 405 (FIG. 4) is combined with an air-puff tonometer measuring unit 301/401 and a camera 329/429 which records medication administration onto the eye. Both modalities can be executed simultaneously, sequentially, or each separately in one simple process step.

In both of these cases, medication is administered by spraying (via non-contact drug administration unit 322/422) the dosed drug from the multi-dose cartridge 305 or the unit-dose cartridge 405 onto the cornea of the eye.

Some functionalities enabled by these two air-puff tonometer embodiments are listed in Table 2 of FIG. 10. For example, both support simultaneous or separate (e.g., sequential) IOP measurement and drug delivery operation. This may be achieved by use of separate medication cartridge and IOP measurement channels. Both support communication with a Smart phone, tablet computer, smartglasses, and/or other computing device for two way real-time or near real-time data transfer between a health care provider, patient, and/or third party. Both may provide a reminder mechanism to alert a patient to a prescheduled medication application or IOP measurement operation. Both provide mechanisms for different medication type selection, and for different dosing options. Both embodiments provide a counter to track medication intake/application, a mechanism for proof of delivery of medication, precision dosage, mechanism for proof of patient ID (e.g., such as by use of a cartridge license ID and/or a camera), and an mechanism to trigger automatic medication application while eye is open (e.g., such as by use a camera to monitor the open/close state of an eye).

Figure 5:
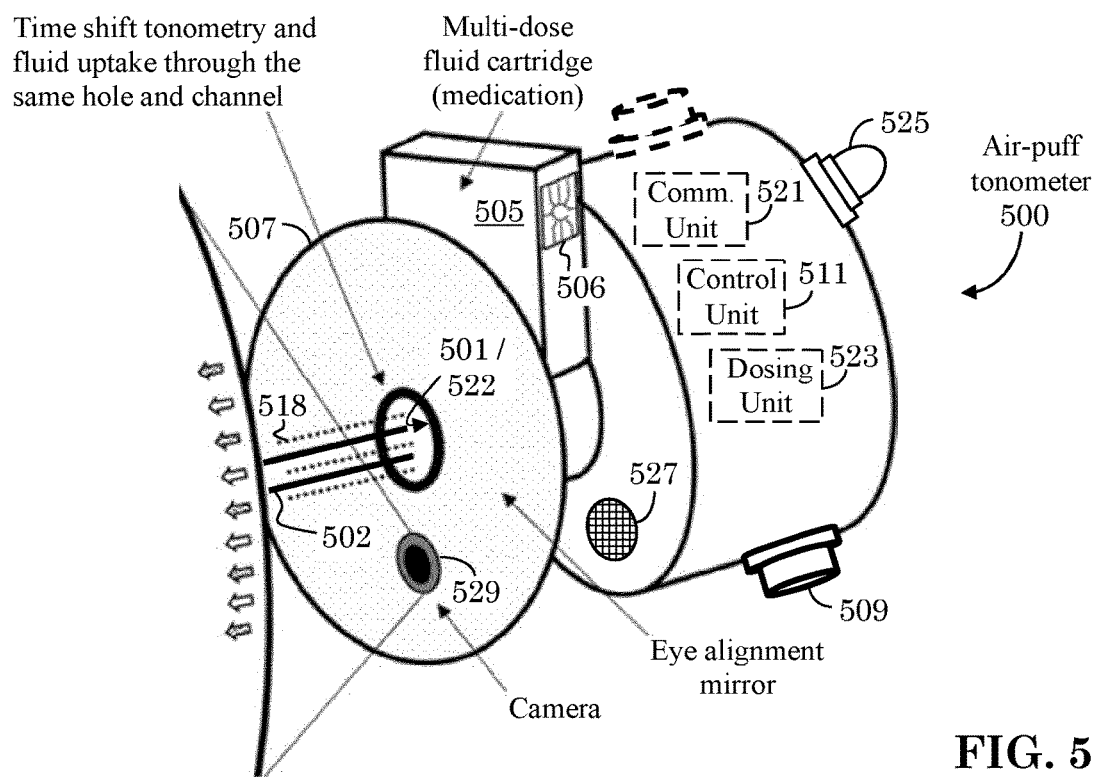
FIG. 5 illustrates an air-puff tonometer with an integrated medication application unit that uses the tonometer's own air-puff and a multi-dose smart cartridge for glaucoma medication application, including a cartridge license key mechanism.

FIG. 5 illustrates an alternate embodiment of an air-puff tonometer 500 combines non-contact drug administration unit 522 with the air-puff tonometer measuring unit 501. That is, the puff of air 502 of the air-puff tonometer measuring unit 501 that is used for measuring IOP is also used for medication application by spraying the medication/drug 518 from a multi-dose cartridge 505 (or alternatively from a unit-dose cartridge) onto the cornea of the eye.

The present combination device 500 for tonometric measurements and drug application on the eye may include an air-puff tonometer measuring unit 501, a drug reservoir 505, a dosing unit 523 (if requested/needed), a concave mirror as alignment unit 507, at least one control button 509 for triggering the measurement and drug application, and a control unit 511 with a memory for storing data of the measurements and/or medication and a memory for storing a treatment plan for the measurements and the medication. The combination device 500 may additionally have a visual unit 525 and/or audible unit 527 for prompting of the patient to carry out a planned measurement and drug administration.

Furthermore, the combination device 500 may also have a camera unit 529 for identifying the patient, his right and left eye, for controlling the orientation of the combination device 500 to the eye and/or for controlling a suitable state of the eye for the measurement and drug administration. Combination device 500 may also have a communication unit 521 for transferring the data stored in the control unit 511. Communication unit 521 may be based on wired or wireless communication for interfacing with personal computers, tablet computer, mobile memories, mobile/smart telephones, and/or smart-glasses.

In the present example, the drug reservoir is a multi-dose cartridge 505, so that an additional dosing unit 523 is required. The multi-dose smart cartridge 505 may be used for glaucoma medication application and may include a cartridge license key mechanism 506.

Alternatively, the drug reservoir may be a standard medication bottle. In this case, an additional dosing unit may be required.

Figure 6:
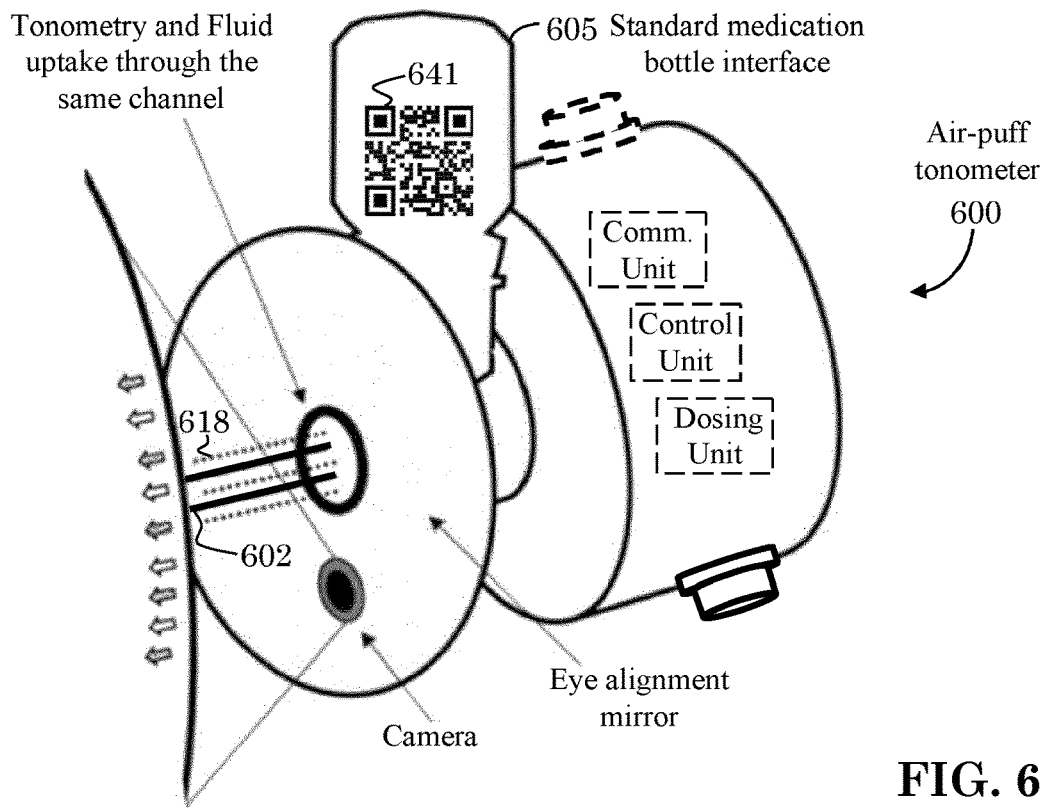
FIG. 6 illustrates an air-puff tonometer with an integrated medication application unit that uses the tonometer's own air-puff and a standard medication bottle for glaucoma medication application including an interface.

FIG. 6 illustrates an alternate embodiment of an air-puff tonometer 600 that uses a standard medication bottle 605 for application of glaucoma medication 618 by application of a puff of air 602, as described above. A quick response code (QR Code) 641 or other identification means (such as a radio frequency identification (RFID) or barcode) may be used as an interface for the standard medication bottle 605 for glaucoma medication application. All other elements are similar to other air-puff tonometers described above.

Figure 7:
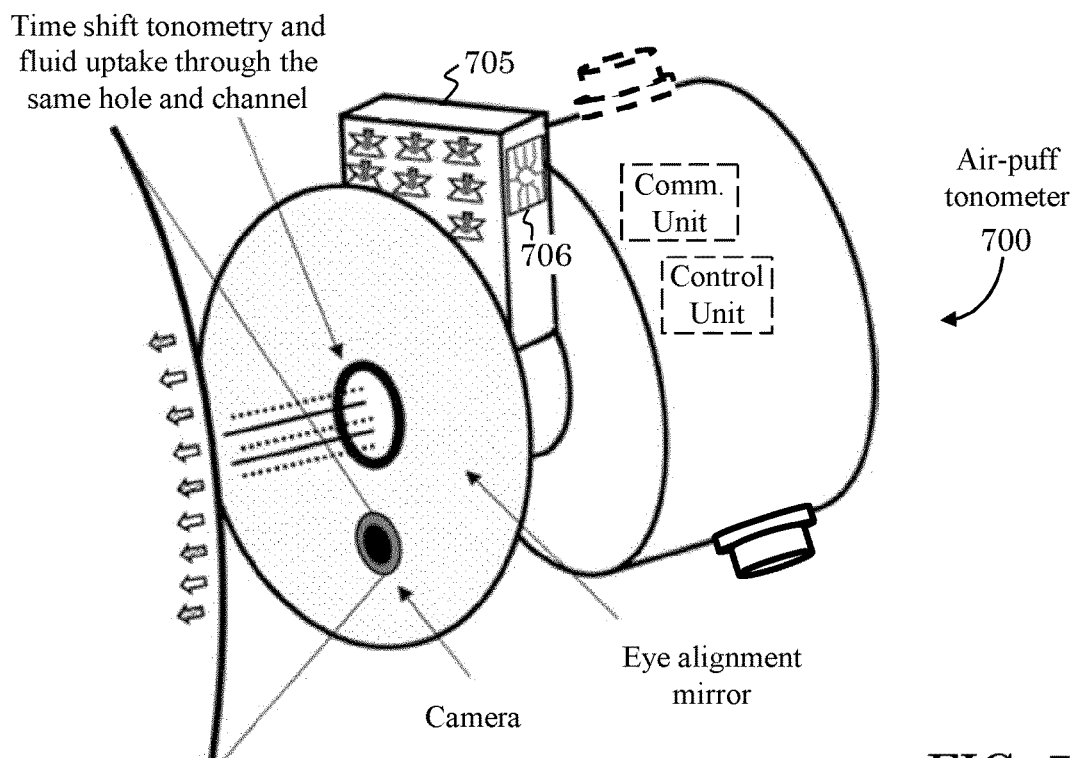
FIG. 7 illustrates an air-puff tonometer with an integrated medication application unit that uses the tonometer's own air-puff and a unit-dose smart cartridge for glaucoma medication application including a cartridge license key mechanism.

In another embodiment of the present invention, illustrated in FIG. 7, the drug reservoir is a unit-dose smart cartridge 705, so that a dosing unit is not required. Unit dose medication has the advantage of allowing preservative free drugs.

FIG. 7 illustrates an air-puff tonometer 700 with unit-dose smart cartridge 705 for glaucoma medication application including a cartridge license key mechanism 706. All other elements of the present embodiment are similar to the air-puff tonometers described above.

In the above examples, a multi-dose cartridge (e.g., FIG. 5), a standard medication bottle interface (e.g., FIG. 6), or a unit-dose smart cartridge with single doses (e.g., FIG. 7) is combined with an air-puff tonometer using the same delivery channel for both IOP measurement and medication application (e.g. the same air puff delivery mechanism is used for both IOP measurement and medication application).

This may be achieved, for example, by using a drop release mechanism that is timed with the air-puff stream to deliver an air-puff for both IOP measurement and medication onto the eye (e.g., simultaneously using a single air-puff or sequentially using sequential air-puffs). That is, the air-puff process steps (e.g., air-puff application mechanism) can be executed either with or without medication release, such as, for example, by use of a smart scheduler application/method or mechanism.

Figure 8A:
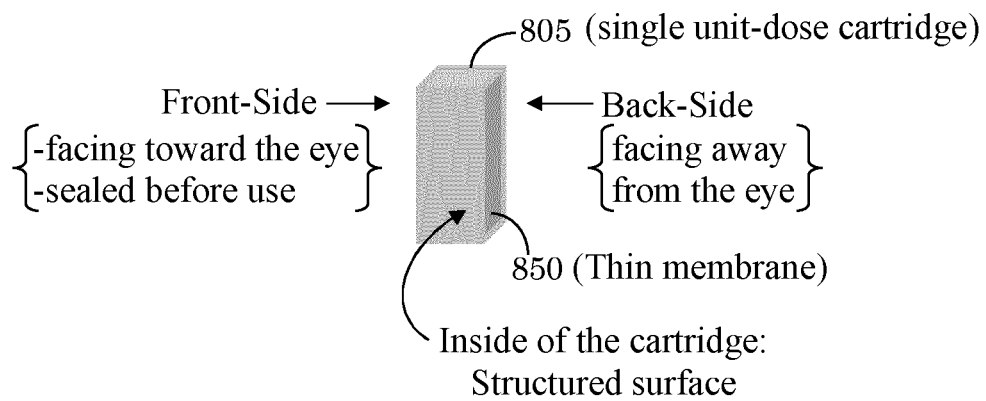
FIG. 8A illustrates a sealed single-dose cartridge for medication delivery.

FIG. 8A illustrates an alternate design of a single, unit-dose smart cartridge 805 for drug delivery to an eye. FIG. 8A shows unit-dose smart cartridge 805 as it may appear when not loaded into an air-puff tonometer. It is to be understood that multiple unit-dose (or single-dose) cartridges may be configured (e.g. loaded) into a magazine and loaded, as a group, into a tonometer. The front side of the unit-dose cartridge 805 (e.g., the side facing the eye) may be sealed until medication is to be applied to the eye. That is, the front side may be unsealed by the triggering of a medication release action, so that the medication is delivered to the eye. Preferably, the unit-dose cartridge 805 has a thin membrane 850 on its back-side (e.g., the side facing away from the eye). The inside of the unit-dose cartridge 805 may have a structured surface configured for drug (medication) storage and/or release. The drug may be stored within unit-dose cartridge 805, e.g., on the opposite side of the thin membrane 850, and when an air-puff (or a retractable probe/arm or other force-applying mechanism) hits (or presses against) the thin membrane 850, the membrane 850 is deformed causing the drug within the cartridge 805 to be released (e.g., pushed and/or sprayed) out of the front side of cartridge 805 towards the eye.

Figure 8B:
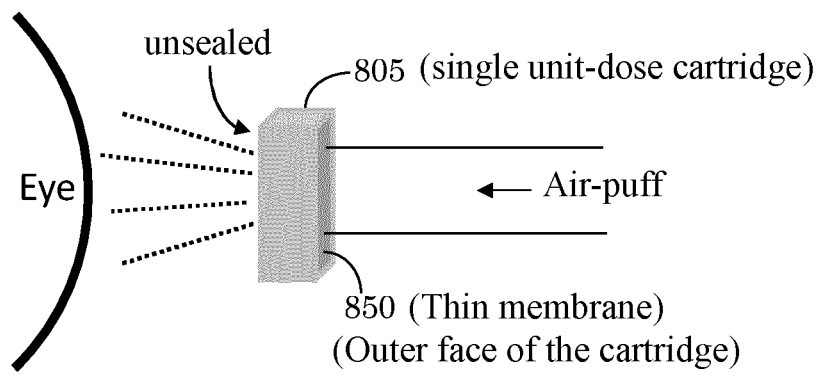
FIG. 8B illustrates a single-dose cartridge that is unsealed by a trigger for medication release, so that the medication can delivered.

FIG. 8B illustrates the single-dose cartridge 805 of FIG. 8A in an unsealed state so that medication can be delivered to an eye by an applied force (e.g. an applied air-puff).

In response to triggering a medication release operation, the single dose cartridge is unsealed so that medication can be delivered to an eye. The membrane surface side within the cartridge can either be structured physically or chemically, such that the medication/drug can be placed on this membrane side. The layout of the structuring is designed such that an optimal fluid delivery to the eye can be achieved. Having such a cartridge design no contact to the air puff channel exists and sterility can be ensured. A further advantage is that the present approach uses only as much medication fluid as the eye can absorb.

Alternatively, the unit-dose cartridge 805 may have a material inside that has a porous or a grid structure. In this case, both front and back sides of cartridge 805 would have to be unsealed for use, so that the medication could be delivered by an air-puff.

The single dose cartridges may be arranged in a magazine and may be loaded to the air puff channel. During a tonometry measurement operation, an empty position of the magazine may be used, e.g., if no medication is to be applied during the taking of the tonometry measurement.

FIG. 11 illustrates a Table 3 that lists some functionalities supported by the above-described air-puff tonometers that use the same air-puff channel and mechanism for both tonometry measurement and medication application. For example, these configurations support both simultaneous or separate (e.g., sequential) IOP measurement and drug delivery operation, such as by use of a Medication-Intake and/or IOP selector. The present configurations support communication with a Smart phone, tablet computer, smart-glasses, and/or other computing/electronic device for two-way, real-time or near real-time data transfer between a health care provider, patient, and/or third party. A reminder mechanism may be provided to alert a patient to a prescheduled medication application or IOP measurement operation. Mechanisms may be provided for different medication type selection, and for different dosing options. Also supported by the present embodiments are a counter to track medication intake/application and mechanisms for proof of delivery of medication, precision dosage, proof of patient ID (e.g., such as by use of a cartridge license ID and/or a camera), and automatic triggering of medication application while an eye is opened (e.g., such as by use a camera to monitor the open/close state of an eye).

In addition to housing both a tonometric measuring unit (for acquiring an intraocular pressure (IOP) measurement for the eye) and a drug administration unit (for applying a drug/medication to the eye), the above-discussed combination devices further provide mechanisms (e.g., control unit, storage unit, communication unit, smart phone, tablet computers, etc.) for monitoring adherence to drug application (e.g., adherence to a treatment plan), and for monitoring the effectiveness of drugs and their dosages. These mechanisms may be expanded to provide health care providers with additional information to better control the medication dosages and types of medications prescribed to a patient.

FIG. 12 illustrates another embodiment of a combination device 1200 for tonometry and drug administration along with an example application 1272A for improved monitoring of IOP measurements and for better assessment of a medication's effectiveness. In the present example, the tonometer is embodied within a "cap" 1280 that attaches to a medication bottle (or cartridge/drug reservoir) 1205. In the present example, medication bottle 1205 (with optional QR Code 1241) is a standard eye-drop bottle that delivers medication as drops 1218. The present tonometer 1200 takes tonometry measurements in contact-free manner, and thereby minimizes sterility issues. The present example preferably uses ultrasound to acquire IOP measurements, but it is to be understood that any of the above-described non-contact methods may optionally be used.

In FIG. 12, one or more ultrasound transducers 1201 (or transceivers) may be positioned on (or within) the cap 1280 such that when the cap 1280 is attached to medication bottle 1205, the ultrasound transducers 1201 are positioned along (e.g. surrounding or along the perimeter of) the opening of medication bottle 1205. Ultrasound transducers 1201, which may be miniaturized ultrasound transducers, convert received control signals into acoustic waves that impart a force onto the cornea 1219 of the eye and induce a deformation of the cornea 1219 and/or mechanical waves on the cornea 1219. This mechanical distortion on the cornea may then be observed by the tonometer 1200 (e.g., by use of a transceiver, camera, light detector, optical interferometer, etc. as discussed above) to obtain an IOP measurement. Preferably, tonometer 1280 includes a wireless communication device (e.g., RFID, Bluetooth, Wi-Fi, etc.) for (bidirectional) communication (e.g., by transfer of radio signals) with a remote computing device 1270, which may be a hand-held computing device such as a smart phone or tablet computer running a software drug management application (e.g., a "drug management app" 1272A/1272B). Optionally, some of the above-described tasks of a tonometer in accord with the present invention (e.g., data processing and data storage) may be off-loaded from tonometer 1280 onto remote computing device 1270 so that the number of need components in tonometer 1280 may be reduced. Optionally, the remote computing device 1270 may have an attachable (or built-in) wireless energy transmitter 1274 for wirelessly powering the tonometer 1200, such that tonometer 1280 may operate without the use of batteries or other dedicated power supply.

Thus, tonometer 1280 effectively constitutes a contact-free, miniaturized, ultra-sound-based tonometry device embodied within a tonometry-cap (with an ultrasound-transducer array) for a drug delivery bottle 1205. Tonometer 1280 may be reused by being transferred from one bottle 1205 to another. Alternatively, every eye drop bottle 1205 may be equipped with its own tonometer-cap (e.g., "tono cap").

Preferably, the drug management app 1272A may be configured to improve tonometry measurements presented to a health-care provider and to rate the effectiveness of specific medications. A healthcare provider typically considers no more than one IOP measurement per day when reviewing a patient's IOP history. It has been found, however, that the information reviewed by the healthcare provider might not be optimal. Aside from an intrinsic error in all IOP measurements, a person's intraocular pressure may vary throughout the day, such that a single IOP measurement for the day might not be a good representations of the patient's daily IOP condition. It has further been observed that a medication's effectiveness at reducing IOP may decrease over time. There may be multiple reasons for a medication's reduced effectiveness. For example, medication drops may induce a change in the tissue (e.g., conjunctiva scarring, etc.), so that the tissue's reaction to the medication may change (e.g. reduce) over time. Another reason may be that a patient might not respond to one type of action mechanism at all, such that the patient is a "non-responder" (or limited responder) to a particular medication. Consequently, if a healthcare provider observes an increasing trend in IOP, it may not be possible to determine if the IOP increase is due to a further reduction in an eye's capacity for aqueous drainage, or due to a drug not being effective anymore (or being of reduced effectiveness), particularly if a patient is taking multiple different medications. The above-described combination device(s) and drug management app can help address these issues.

Typically, a patient takes a single IOP measurement within a one day period, such as in the morning. However, a person's IOP can change during the day, such as due to changes in aqueous production. However, a patient's treatment may require application of medication multiple times per day, such as morning, noon, and evening. A preferred embodiment may automatically take an IOP measurement each time medication is applied. That is, an input signal to the combination device to apply medication, may trigger an automatic IOP measurement as well. Consequently, the present combination device would record multiple IOP measurements per day e.g., three measurements per day (morning, noon, evening), which may be combined (e.g., by averaging) to provide the healthcare provider with a more meaningful (representative) IOP measurement for the day. For example, although each IOP measurement may have an intrinsic measurement error, averaging multiple IOP measurements at different times of the day may reduce the overall error measurement, while providing a more representative IOP measure for the day.

With reference to FIG. 13, the present combination device(s) (and/or drug management app 1272A/1272B) may monitor and compare IOP measurements and applied medication dosages (along the same time reference) to help determine the efficacy of specific medication types and dosages. The remote computing device 1270 may generate a plot of tonometry readings (e.g., measurements) versus time and a plot of drug dosage versus time for each applied medication. In the present example, three drug dosage versus time plots 1273, 1275 and 1277 are shown for three different medications, Med_A, Med_B and Med_C, respectively. This information may be provided in a summary section SUM1 of app 1272A/1272B. This approach helps to better determine how intraocular pressure changes in the presence or absence (e.g., increase or decrease) of multiple medications. A reduction in medication dosage may be intentional (e.g., prescribed) or unintentional (e.g., a patient neglects to administer medication and/or applies an incorrect dosage). To illustrate this feature, an exemplary case is provided.

In the exemplary case, a patient initially takes only drug Med_A. If a healthcare provider observes an increase in intraocular pressure, the healthcare provider may add drug Med_B, and later add a third drug Med_C to keep the IOP down. Med_A, Med_B, and Med_C may have different IOP lowering mechanisms (e.g., prostaglandins, beta blockers, etc.). As explained above, a medication may lose its effectiveness (e.g., wear off) over time. For example, Med_A may have lost its effectiveness by the time Med_C was added, but it may happen that no one noticed the change in effectiveness of Med_A so that the patient continues to take Med_A to little benefit. The present invention helps to identify these changes in medication efficacy.

For example, if the patient had previously run out of Med_A for a few days, or simply forgot to apply it, then the present invented system for combined monitoring of drug usage and IOP measurement would have noticed that measured IOP was not reacting to the omitted drug Med_A. That is, the exclusion of Med_A had little effect (e.g., within a predefined range or percentage of an observed norm or running average) on the measured IOP. This would indicate that drug Med_A may no longer be effective for the specific patient. The healthcare provider would then be informed (e.g., alerted by email or in summary SUM1) of this possible change in effectiveness, such by SUM1. The healthcare provider may then chose to remove Med_A from the patient's treatment plan and relieve the patient from any side effects associated with Med_A, such as stinging, dry eye, redness, eye lash growth, etc.

Another example may be if the patient later forgets to take Med_B, and this results in a large effect on IOP (e.g., greater than a predefined range or percentage increase), even if the patient is still taking Med_C. This may indicate that Med_B is more effective than Med_C for the particular patient. Again, the healthcare provider would be informed of the strong effect of taking (or omitting) Med_B. The healthcare provider may then chose to increase the dosage of Med_B, and perhaps remove Med_C from the patient's treatment plan. This may be of help to the patient, particularly if Med_C has stronger side effects than Med_B and/or taking Med_C places an economic burden on the patient. This may also reduce the chances of the patient developing a resistance to Med_C (e.g., become non-responsive, or a "non-responder," to Med_C).

Thus, the present invention is able to take advantage of happenstance to better adapt a treatment plan to a specific patient. That is, the present invention can take advantage of the patient occasionally forgetting medication drops (or inadvertently increasing or decreasing the applied dosage), and makes use of the observed, corresponding IOP reaction. This approach also permits a healthcare provider to intentionally modify a patient's treatment plan, and to use the resulting changes in observed IOP to revise the risk/benefit ratio of select medications.

As stated above, the present combination device may be coupled with one or more software applications 1272A/1272B. One application (or application interface) 1272A may be tailored for a doctor's use, and another 1272B may be designed for a patient's use. The doctor's interface 1272A would need to be comprehensive, but still provide quick summaries of various information, such as by use of summary section SUM1, which may include textual information and plots 1271-1277. For example, the summary section SUM1 may include an IOP curve 1271A (e.g., a plot of individual, daily IOP averages or a running IOP average), min-max bands 1271B (e.g., a graphical display, plot, and/or numerical values), sliding average values, etc. Summary section SUM1 may also specify a percentage of medication use adherence for variable filter criterions, such as per medication type, e.g., "drug Med_A→40% adherent", "Med_B→use in morning: 60% adherent", "Med_B→use in evening: 10% adherent," etc. The above mentioned IOP response to individual drugs may also be included in the summary, such as, "Med_A→provides 75% of IOP-lowering effect" or "Med_B→Warning: Non-responder for drug Med_B!."

The app interface 1272B for patients should have a quick, immediate response about where they stand and whether a specific mediation application or IOP measurement was successful, plus provide basic instructions. For example, for time slots (morning, midday, evening) checkmarks CK1 could represent proper use of drops, and/or crosses X1 could represent improper use of drops. Additionally, gamification aspects could be used to help increase patient motivation to adhere to a treatment plan by providing coaching feedback, such as statements like: "Congrats: With 95% medication use adherence, you belong to the top 10% of patients in your age group". Adherence percentage (evaluated per time interval, like day, week, month) could be also displayed as trend curve/plot 1271C.

Figure 14:
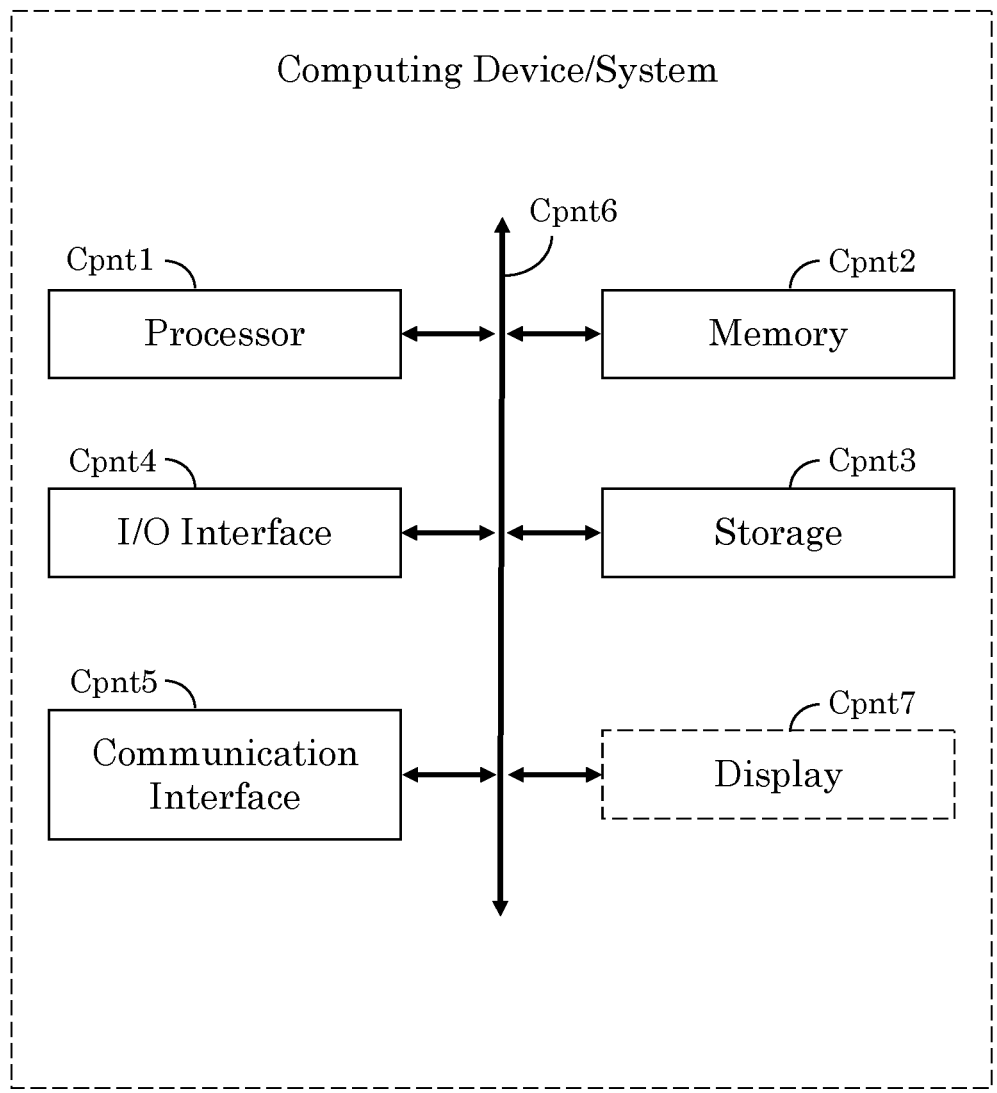
FIG. 14 illustrates an example computer system (or computing device or computer device).

FIG. 14 illustrates an example computer system (or computing device or computer device) suitable for remote computing device 1270 (and optionally for at least parts of the combination device configurations described above). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number internal registers and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to computer system, and include one or more of a disk drives (e.g., hard disk drive, HDD, or solid state drive, SSD), flash memory, ROM, EPROM, optical disc, a magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications and variations will be apparent in light of the foregoing description. The invention described herein is intended to embrace all such alternatives, modifications, applications and variations as may fall within the spirit and scope of the appended claims.

We claim:

1. A combination device for tonometric measurement and drug application on an eye, comprising:
   a device enclosure housing a tonometric measuring unit for acquiring an intraocular pressure (IOP) measurement of the eye and a drug administration unit for applying a drug to the eye;
   a drug reservoir attachable to the device enclosure, wherein the drug administration unit controls the withdrawal of a drug from the drug reservoir for application to the eye; and
   a communication unit for establishing a communication link to an external electronic device, and for exchanging information between the combination device and the external electronic device;
   wherein:
   the combination device includes a dosage monitoring unit that obtains a measure of the amount of drug applied to the eye; and
   the external electronic device includes an electronic data processor that determines an effectiveness-measure of individual drugs based on their applied dosage and consequent effect on monitored IOP measurement.

2. The combination device of claim 1, further comprising:
   a camera positioned to monitor the eye, wherein the drug administration unit automatically applies drug to the eye in response to the eye being in an opened state as determined based on the camera.

3. The combination device of claim 1, further comprising:
   a camera positioned to monitor the eye, wherein the control unit limits the operation of the tonometric measuring unit or the drug administration unit to only when the eye is in an opened state as determined based on the camera.

4. The combination device of claim 1, further comprising:
   a camera positioned to monitor the eye, wherein the combination device identifies a patient based on images from the camera.

5. The combination device of claim 1, further comprising:
   a camera positioned to monitor the eye, wherein the combination device identifies the eye as being a left eye or a right eye based on images from the camera.

6. The combination device of claim 1, further comprising:
a camera positioned to monitor the eye when the tonometric measuring unit is actively obtaining the IOP measurement or the drug administration unit is actively applying the drug to the eye; and
a control unit that, based the camera, records whether the eye was opened or closed during at least one of the tonometric measuring unit obtaining the IOP measurement or the drug administration unit applying the drug.

7. The combination device of claim 1, further comprising:
a user-actuatable control input, wherein both the tonometric measuring unit and drug administration unit are responsive to the same user-actuatable control input.

8. The combination device of claim 7, wherein the tonometric measuring unit and drug administration unit are activated simultaneously in response to the same user-actuatable control input.

9. The combination device of claim 7, wherein the tonometric measuring unit and drug administration unit are activated sequentially in response to the same user-actuatable control input.

10. The combination device of claim 1, wherein:
medication application is activated in response to a medication-application control input; and
the medication-application control input additionally automatically triggers the acquisition of a tonometry measurement.

11. The combination device of claim 1, further comprising:
a memory unit storing at least one of the IOP measurement from the tonometric measuring unit, a drug dosage applied by the drug administration unit, time of day when an IOP measurement or drug is applied, and a treatment plan.

12. The combination device of claim 1, wherein the electronic data processor issues an alert in response to an individual drug having a determined effectiveness measure less than a first predefined threshold or greater than a second predefined threshold higher than the first predefined threshold.

13. The combination device of claim 1, wherein the electronic data processor determines a daily IOP measurement by combining multiple IOP measurements taken at different parts of the same day.

14. The combination device of claim 1, wherein the external electronic device includes an electronic screen that displays a plot of tonometry measurements versus time or a plot of drug dosage versus time.

15. The combination device of claim 1, wherein the external electronic device is one of a personal computers, tablet computer, mobile memory, mobile phones, or smartglasses.

16. The combination device of claim 1, further comprising:
a visual display or audio unit to convey treatment information to a user.

17. The combination device of claim 1, further comprising an alignment unit including a concave mirror to align at least one of the tonometric measuring unit and drug administration unit to the eye, the concave mirror being positioned to provide a reflection of the eye visible to a patient during acquisition of a tonometric measurement or during application of the drug on the eye.

18. The combination device of claim 1, wherein:
the tonometric measuring unit is a dynamic-contact tonometric measuring unit that induces a mechanical response on the cornea of the eye by impacting the cornea with a mechanical probe;
the probe is an integral part of the drug administration unit; and
the probe has access to the drug reservoir, and selectively transfers the drug from the drug reservoir to the eye by impacting the eye.

19. The combination device of claim 18, wherein the drug reservoir is an integral part of the probe.

20. The combination device of claim 19, wherein the probe includes a puncturing mechanism for selectively puncturing the drug reservoir to withdraw the drug and transfer the drug to an eye-impacting part of the probe.

21. The combination device of claim 18, wherein:
the probe has a tip for impacting the cornea;
the drug reservoir is housed within the probe; and
drug is selectively transferred from the drug reservoir to the tip of the probe.

22. The combination device of claim 18, wherein the probe includes a bladder for impacting the cornea, and the bladder is the drug reservoir.

23. The combination device of claim 18, wherein the drug from the reservoir is automatically transferred to the surface of the probe upon the tonometric measuring unit finishing the acquisition of the intraocular pressure (IOP) measurement.

24. The combination device of claim 1, wherein:
the tonometric measuring unit is a dynamic-contact tonometric measuring unit that induces a mechanical response on the cornea of the eye by impacting the cornea with a mechanical probe; and
the drug administration unit is a non-contact drug administration unit that ejects the drug to the cornea of the eye.

25. The combination device of claim 1, wherein:
the tonometric measuring unit is a non-contact tonometric measuring unit including a mechanism for inducing a mechanical response on the cornea of the eye by one of an applied electromagnetic wave, sound wave, air discharge; and
the drug administration unit is a non-contact drug administration unit.

26. The combination device of claim 25, wherein:
the non-contact tonometric measuring unit has an air-applicator opening for applying a puff of air to the eye;
the drug administration unit sprays the drug to the eye through the air-applicator opening of the non-contact tonometric measuring unit.

27. The combination device of claim 1, wherein:
the drug reservoir has a cappable drug-dispersing opening; and
the device enclosure is embodied within a cap for capping the drug-dispensing opening of the drug reservoir.

28. The combination device of claim 27, wherein the drug reservoir is a standard medication bottle.

29. The combination device of claim 28 wherein the cap includes one or more ultrasound transducers to induce a mechanical distortion on the cornea of the eye.

30. The combination device of claim 1, wherein the tonometric measuring unit is one of a rebound tonometer, an air-puff tonometer, or a tonometer based on optical coherence elastography (OCE).

31. The combination device of claim 1, wherein the drug reservoir is one of a single-dose cartridge, a unit-dose cartridge, a multi-dose cartridge, or a standard medical bottle.

32. The combination device of claim 1, wherein the drug reservoir is one of a multi-dose cartridge or standard bottle, said device further comprising:
a dosing unit for controlling an amount of drug applied to the eye.

33. The combination device of claim 1, further comprising two control buttons for respective, separate triggering of tonometric measurement and drug administration.

34. The combination device of claim 1, further comprising a unit for visual or audible prompting of the patient to carry out a planned measurement or drug administration.

35. The combination device of claim 1, further comprising a covering unit for covering or enclosing at least the parts of the combination device that come into contact with the eye during tonometry measurement or medication application.

36. The combination device of claim 1, further comprising a cleansing unit for rinsing and/or sterilizing parts of the combination device that come into contact with the eye.

37. A combination device for tonometric measurement and drug application on an eye, comprising:
a device enclosure housing a tonometric measuring unit for acquiring an intraocular pressure (IOP) measurement of the eye and a drug administration unit for applying a drug to the eye;
a drug reservoir attachable to the device enclosure, wherein the drug administration unit controls the withdrawal of a drug from the drug reservoir for application to the eye;
a dosage monitoring unit that obtains a measure of the amount of drug applied to the eye; and
an electronic data processor that determines an effectiveness-measure of individual drugs based on their applied dosage and consequent effect on monitored IOP measurement.

38. The combination device of claim 37, wherein the electronic data processor issues an alert in response to an individual drug having a determined effectiveness measure less than a first predefined threshold or greater than a second predefined threshold higher than the first predefined threshold.

39. The combination device of claim 37, wherein the electronic data processor determines a daily IOP measurement by combining multiple IOP measurements taken at different parts of the same day.

40. A system for tonometric measurement and drug application on an eye, comprising:
a device enclosure housing a tonometric measuring unit for acquiring an intraocular pressure (IOP) measurement of the eye and a drug administration unit for applying a drug to the eye;
a drug reservoir attachable to the device enclosure, wherein the drug administration unit controls the withdrawal of a drug from the drug reservoir for application to the eye;
a dosage monitoring unit that obtains a measure of the amount of drug applied to the eye; and
an electronic data processor that determines an effectiveness-measure of individual drugs based on their applied dosage and consequent effect on monitored IOP measurement.

41. The system of claim 40, wherein the electronic data processor issues an alert in response to an individual drug having a determined effectiveness measure less than a first predefined threshold or greater than a second predefined threshold higher than the first predefined threshold.

42. The system of claim 40, wherein the electronic data processor determines a daily IOP measurement by combining multiple IOP measurements taken at different parts of the same day.

* * * * *

UNITED STATES PATENT AND TRADEMARK OFFICE
CERTIFICATE OF CORRECTION

PATENT NO.        : 12,295,661 B2                              Page 1 of 1
APPLICATION NO.   : 17/047346
DATED             : May 13, 2025
INVENTOR(S)       : Rudolf Von Bünau It is certified that error appears in the above-identified patent and that said Letters Patent is hereby corrected as shown below:

On the Title Page
Item (73) Assignee, Please change "Carl Zeiss AG" to --Carl Zeiss Meditec AG--.

Signed and Sealed this
Fifteenth Day of July, 2025

Coke Morgan Stewart
*Acting Director of the United States Patent and Trademark Office*